US010024837B2

(12) United States Patent
Yamashita

(10) Patent No.: US 10,024,837 B2
(45) Date of Patent: Jul. 17, 2018

(54) DETERIORATION DETERMINATION APPARATUS AND DETERIORATION DETERMINATION METHOD

(71) Applicant: HONDA MOTOR CO., LTD., Tokyo (JP)

(72) Inventor: Toru Yamashita, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 288 days.

(21) Appl. No.: 14/945,432

(22) Filed: Nov. 19, 2015

(65) Prior Publication Data

US 2016/0169859 A1 Jun. 16, 2016

(30) Foreign Application Priority Data

Dec. 15, 2014 (JP) ................................. 2014-253225

(51) Int. Cl.
*G01N 33/28* (2006.01)
*G01N 25/20* (2006.01)

(52) U.S. Cl.
CPC .......... *G01N 33/2888* (2013.01); *G01N 25/20* (2013.01)

(58) Field of Classification Search
CPC ........................... G01N 33/2888; G01N 25/20
See application file for complete search history.

(56) References Cited

U.S. PATENT DOCUMENTS

| | | | | |
|---|---|---|---|---|
| 6,677,282 B2* | 1/2004 | Lange | .................... | C10L 1/198 44/386 |
| 7,433,770 B2* | 10/2008 | Inagawa | ............. | F16H 57/0405 307/144 |
| 7,581,434 B1* | 9/2009 | Discenzo | ........... | G01N 33/2888 73/53.01 |
| 7,662,881 B2* | 2/2010 | Walton | ................... | C08F 210/16 524/230 |
| 8,105,992 B2* | 1/2012 | Schauder | .............. | C08F 297/08 508/591 |
| 2005/0131599 A1* | 6/2005 | Inagawa | ............. | F16H 57/0405 701/51 |
| 2012/0025529 A1* | 2/2012 | Davis | ...................... | F16N 29/04 290/44 |

(Continued)

FOREIGN PATENT DOCUMENTS

JP 2011-214932 10/2011

*Primary Examiner* — Lisa Caputo
*Assistant Examiner* — Philip Cotey
(74) *Attorney, Agent, or Firm* — Mori & Ward, LLP

(57) ABSTRACT

A deterioration determination apparatus includes an oil temperature detector, an oil temperature rate of increase calculator, a threshold calculator, and a deterioration determination device. The oil temperature detector is configured to detect an oil temperature of oil for lubrication of a transmission in a vehicle. The oil temperature rate of increase calculator is configured to calculate a rate of increase in the oil temperature. The threshold calculator is configured to calculate based on a travel condition of the vehicle a first threshold. The deterioration determination device is configured to compare the rate of increase in the oil temperature with the first threshold. The deterioration determination device is configured to determine that the oil is deteriorated when the rate of increase in the oil temperature is equal to or higher than the first threshold.

18 Claims, 8 Drawing Sheets

(56) References Cited

U.S. PATENT DOCUMENTS

| | | | |
|---|---|---|---|
| 2012/0303230 A1* | 11/2012 | Qiao | G01N 33/1826 |
| | | | 701/59 |
| 2013/0191012 A1* | 7/2013 | Hirotsu | B60W 10/02 |
| | | | 701/113 |
| 2013/0275016 A1* | 10/2013 | Mitani | F16H 61/12 |
| | | | 701/62 |

* cited by examiner

DETERIORATION DETERMINATION APPARATUS AND DETERIORATION DETERMINATION METHOD

CROSS REFERENCES TO RELATED APPLICATIONS

The present application claims priority under 35 U.S.C. § 119 to Japanese Patent Application No. 2014-253225, filed Dec. 15, 2014, entitled "Deterioration Determination Apparatus For Automatic Transmission Fluid." The contents of this application are incorporated herein by reference in their entirety.

BACKGROUND

1. Field

The present disclosure relates to a deterioration determination apparatus and a deterioration determination method.

2. Description of the Related Art

As a feature for determining deterioration of an automatic transmission fluid (ATF, or a transmission oil), a technology described in, for example, Japanese Unexamined Patent Application Publication No. 2011-214932 is known.

The technology described in Japanese Unexamined Patent Application Publication No. 2011-214932 is configured in such a manner that the way of using a vehicle is monitored by acquiring a plurality of deterioration elements related to various deterioration factors which are generated in accordance with traveling of the vehicle and may increase the deterioration of automatic transmission fluid, then the degree of severity of the using mode of the automatic transmission fluid in a transmission mounted in the vehicle is determined in accordance with the deterioration in an estimated value of oil deterioration calculated on the basis of the acquired plurality of deterioration elements, and then a change timing of the automatic transmission fluid is determined in accordance with the degree of severity, and reported.

SUMMARY

According to a first aspect of the present invention, a deterioration determination apparatus includes an oil temperature detector, an oil temperature rate of increase calculator, a threshold calculator, and a deterioration determination device. The oil temperature detector is configured to detect an oil temperature of oil for lubrication of a transmission in a vehicle. The oil temperature rate of increase calculator is configured to calculate a rate of increase in the oil temperature detected by the oil temperature detector. The threshold calculator is configured to calculate based on a travel condition of the vehicle a first threshold for estimating degradation of a defoaming property of the oil. The deterioration determination device is configured to compare the rate of increase in the oil temperature with the first threshold. The deterioration determination device is configured to determine that the oil is deteriorated when the rate of increase in the oil temperature is equal to or higher than the first threshold.

According to a second aspect of the present invention, a deterioration determination method includes detecting an oil temperature of oil for lubrication of a transmission in a vehicle. A rate of increase in the oil temperature is calculated. A first threshold is calculated based on a travel condition of the vehicle. The first threshold is for estimating degradation of a defoaming property of the oil. The rate of increase in the oil temperature is compared with the first threshold. When the rate of increase in the oil temperature is equal to or higher than the first threshold, it is determined that the oil is deteriorated.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE PREFERRED EMBODIMENTS

Figure 1:
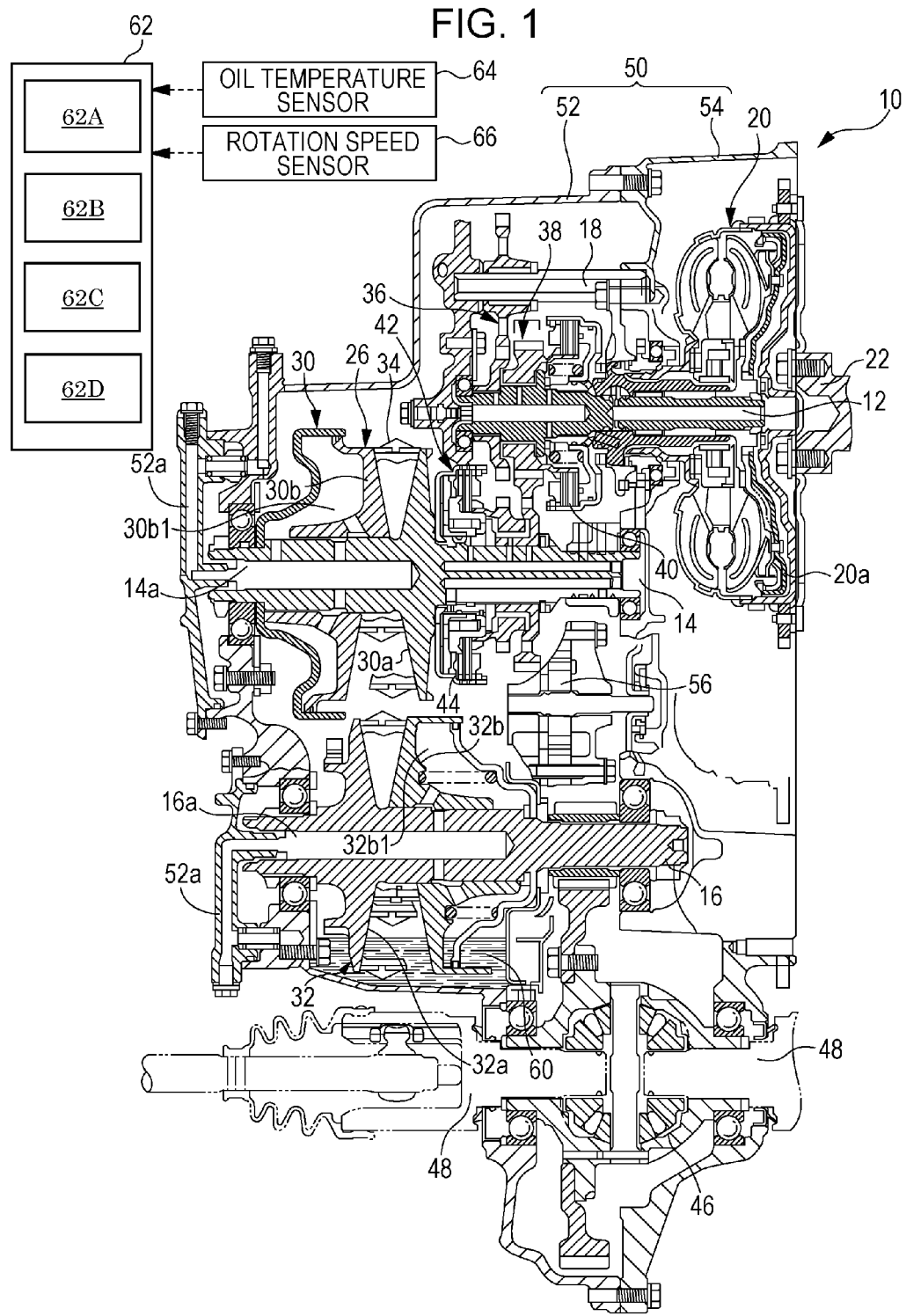
FIG. 1 is a schematic diagram illustrating a deterioration determination apparatus in accordance with an embodiment.

The embodiments will now be described with reference to the accompanying drawings, wherein like reference numerals designate corresponding or identical elements throughout the various drawings.

An embodiment of a deterioration determination apparatus for an automatic transmission fluid will be explained with reference to the accompanying drawings.

Embodiment

FIG. 1 is a schematic diagram illustrating a deterioration determination apparatus for an automatic transmission fluid in accordance with the embodiment.

The symbol 10 in FIG. 1 denotes an automatic transmission (hereinafter referred to simply as "the transmission"). The transmission 10 is mounted in a vehicle (not shown) and changes a speed of output of a driving source, more specifically, an internal combustion engine (hereinafter referred to as "the engine", not shown in FIG. 1) and transmits the changed output speed to right and left drive wheels (not shown).

As illustrated in FIG. 1, the transmission 10 includes an input shaft (rotation shaft) 12, a drive (DR) pulley shaft (rotation shaft) 14, a driven (DN) pulley shaft (rotation shaft) 16, and an idle shaft 18 provided in parallel with each other, and output of the engine is input from the input shaft 12 via a torque converter 20 having a lock-up clutch 20a.

A continuously variable transmission mechanism (hereinafter referred to as "the CVT mechanism") 26 is provided between the DR pulley shaft 14 and the DN pulley shaft 16.

The CVT mechanism 26 is formed of a DR pulley 30 arranged on the DR pulley shaft 14, a DN pulley 32 arranged on the DN pulley shaft 16, and an endless flexible member 34 (such as a metallic V-belt) wound between the DR pulley 30 and the DN pulley 32.

The DR pulley 30 is formed of a fixed DR pulley half-body 30a, which is provided on the DR pulley shaft 14 in such a manner that the fixed DR pulley half-body 30a cannot rotate relative thereto and cannot move in the shaft direction, and a movable DR pulley half-body 30b, which is provided on the DR pulley shaft 14 in such a manner that the movable DR pulley half-body 30b cannot rotate relative thereto but can move in the shaft direction with respect to the fixed DR pulley half-body 30a.

The DN pulley 32 is formed of a fixed DN pulley half-body 32a, which is provided on the DN pulley shaft 16 in such a manner that the fixed DN pulley half-body 32a cannot rotate relative thereto and cannot move in the shaft direction, and a movable DN pulley half-body 32b, which is provided on the DN pulley shaft 16 in such a manner that the movable DN pulley half-body 32b cannot rotate relative thereto but can move in the shaft direction with respect to the fixed DN pulley half-body 32a.

The movable DR pulley half-body 30b and the movable DN pulley half-body 32b are respectively provided with piston chambers (hydraulic operation chambers) 30b1, 32b1, and the movable DR pulley half-body 30b and the movable DN pulley half-body 32b move close to or away from the fixed DR pulley half-body 30a and fixed DN pulley half-body 32a, respectively, according to the hydraulic pressure (lateral pressure) of hydraulic oil supplied to the respective piston chambers 30b1, 32b1.

On the input shaft 12, a forward/reverse switching mechanism 36 that changes the direction of travel of the vehicle is provided. The forward/reverse switching mechanism 36 is formed of a forward (FWD) travel gear 38 and a forward (FWD) clutch 40, and a reverse (RVS) travel gear 42 and a reverse (RVS) clutch 44.

Output of the engine, the output being input from the input shaft 12 via the torque converter 20, is transmitted to the DR pulley shaft 14 via the forward travel gear 38 or the reverse travel gear 42 to cause the DR pulley shaft 14 to rotate in a forward direction or a reverse direction of the vehicle.

A differential mechanism 46 is connected to the DN pulley shaft 16. Right and left axles 48 are fixed to the differential mechanism 46, and drive wheels (not shown) are attached to ends of the right and left axles 48.

In the CVT mechanism 26, by increasing or decreasing the lateral pressure of both the DR pulley 30 and the DN pulley 32, widths of the pulleys are changed and thereby winding radii of the endless flexible member 34 with respect to both pulleys 30, 32 are changed, and thus, a desired gear ratio according to the ratio (pulley ratio) of the winding radii can be obtained steplessly.

As illustrated in FIG. 1, the transmission 10 is housed in a case 50. More specifically, the case 50 is formed of a transmission case 52 that houses a body portion, such as the transmission 10, and a torque converter case 54 that houses the torque converter 20 and so on.

Inside the transmission case 52, a hydraulic (oil) pump 56, which is driven by the engine, is provided to pump up an automatic transmission fluid (ATF) 60 from an oil pan (reservoir) disposed at a lower portion and forcibly feed the ATF 60 to the piston chambers 30b1, 32b1 of the DR and DN pulleys 30, 32.

The DR and DN pulley shafts 14, 16 are formed into hollow shapes, and oil passages 14a, 16a that communicate with the respective piston chambers 30b1, 32b1 are formed respectively inside the DR and DN pulley shafts 14, 16 in the shaft directions thereof. In addition, an oil passage 52a is formed inside a wall of the transmission case 52. The ATF 60 pumped up from the oil pan by the hydraulic pump 56 is forcibly fed (supplied) to the piston chambers 30b1, 32b1 of the DR and DN pulleys 30, 32 via the oil passage 52a in the transmission case 52 and the oil passages 14a, 16a in the DR and DN pulley shafts 14, 16, and is also forcibly fed to a hydraulic control valve (not shown) and piston chambers (not shown) of the forward clutch 40 and the reverse clutch 44.

An electronic control unit (ECU) 62 is provided at an appropriate position of the vehicle.

An oil temperature sensor 64 is provided near the oil pan disposed at the lower portion of the transmission case 52, and outputs signals indicating oil temperature of the ATF 60. A rotational speed sensor 66 is provided near the axle 48 and outputs a pulse signal for every predetermined rotation angle of the axle 48.

Outputs from the oil temperature sensor 64 and the rotational speed sensor 66 are transmitted to the ECU 62. The ECU 62 then measures the time interval of output signals of the rotational speed sensor 66 to detect a vehicle speed (travelling speed of the vehicle).

Various sensors (not shown) other than the oil temperature sensor 64 and the rotational speed sensor 66 are provided, and outputs from the various sensors are also transmitted to the ECU 62. In addition, the ECU 62 is configured so as to be capable of communicating with an engine ECU (not shown) that controls operations of the engine, and the ECU 62 acquires various engine operation parameters, such as engine speed, via the engine ECU.

On the basis of the outputs of the sensors, the outputs being input to the ECU 62, and the engine operation parameters acquired via the engine ECU, the ECU 62 controls an engagement amount of the lock-up clutch 20a of the torque converter 20, the width of a pulley, such as the DR pulley 30, and engagement and disengagement of the forward clutch 40 or the reverse clutch 44 by adjusting the hydraulic pressure supplied to the back pressure chamber, the piston chamber or the like.

Furthermore, the ECU 62 determines deterioration of the ATF 60. A deterioration determination operation (processing) of the ECU 62 for the ATF 60 will be explained below.

Figure 2:
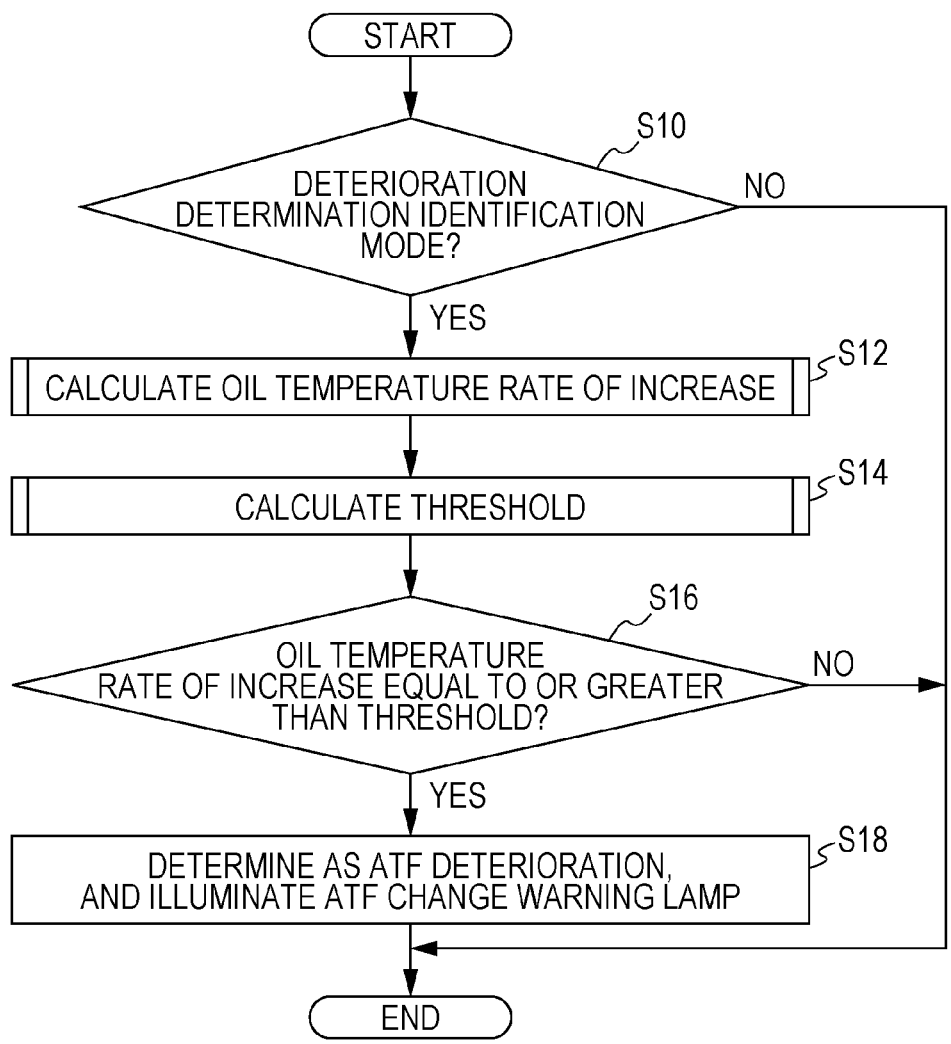
FIG. 2 is a flowchart illustrating operation of the apparatus illustrated in FIG. 1.

FIG. 2 is a flowchart illustrating the operation thereof.

First in step S10, a deterioration determination device 62A in the ECU 62 determines whether or not a mode is a deterioration determination identification mode (S: processing step). The deterioration determination identification mode indicates that a predetermined condition for a mode in which a deterioration determination for the ATF 60 is possible (allowed) is established.

Figure 3:
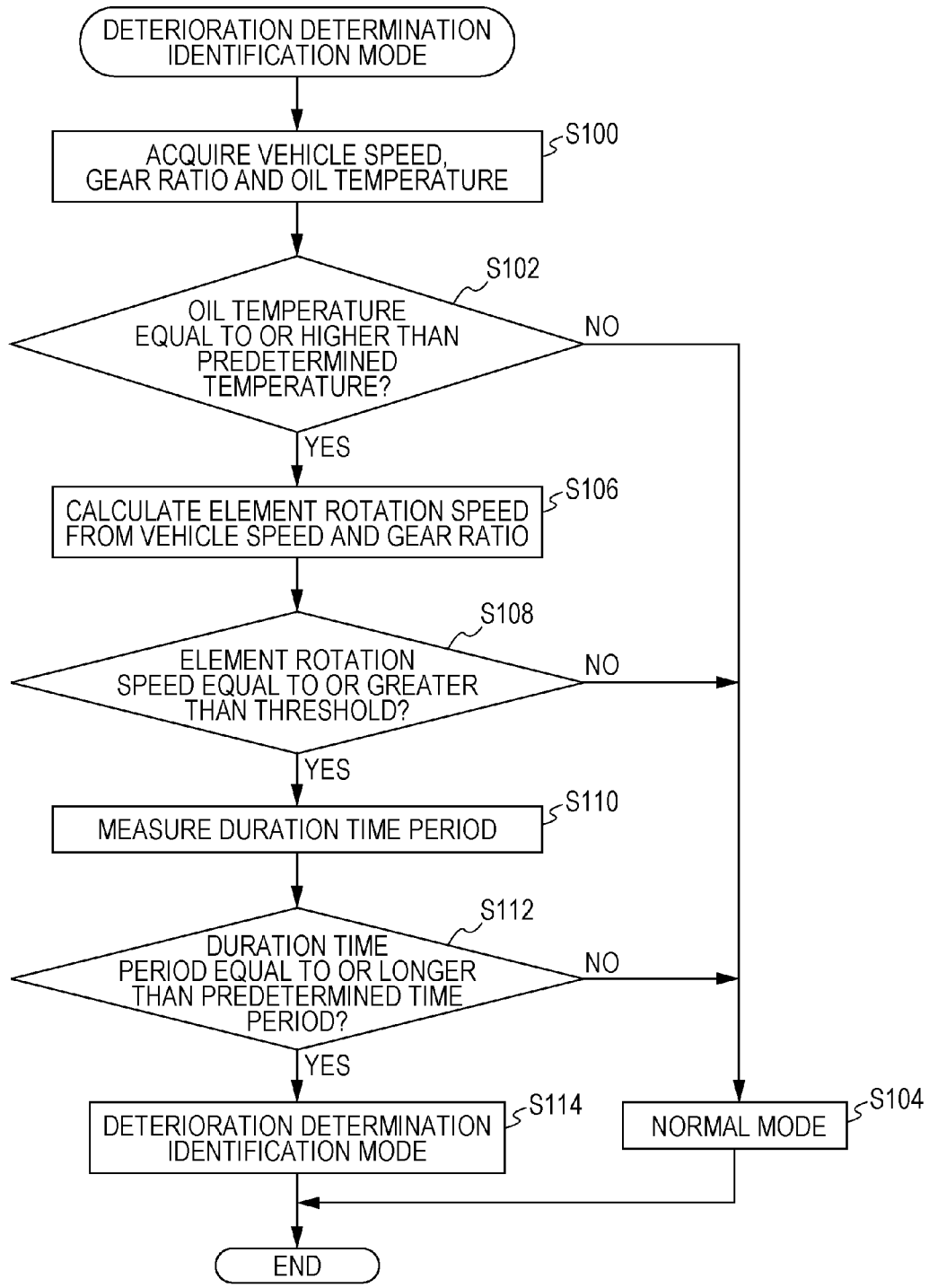
FIG. 3 is a subroutine flowchart of the flowchart of FIG. 2, illustrating processing for determining whether or not a mode is a deterioration determination identification mode.

FIG. 3 is a subroutine flowchart illustrating determination processing for determining whether or not a mode is a deterioration determination identification mode.

First, in step S100, the vehicle speed detected by the rotational speed sensor 66, the gear ratio currently set in the CVT mechanism 26, and the oil temperature of the ATF 60 detected by the oil temperature sensor 64 are acquired (read).

Then, the process proceeds to step S102 to determine whether or not the detected oil temperature is equal to or higher than a predetermined temperature, and if NO, the process proceeds to step S104 to determine that the mode is a normal mode and not the deterioration determination identification mode.

Meanwhile, if YES in step S102, the process proceeds to step S106 to search a predetermined property from the vehicle speed and the gear ratio and calculate an element rotation speed.

Figure 4:
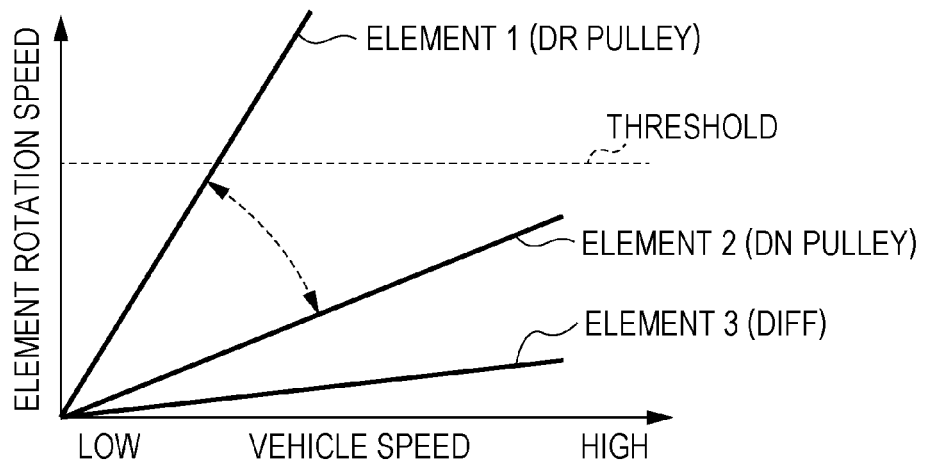
FIG. 4 is an explanatory drawing for the properties used in calculating the element rotation speed in FIG. 3.
Figure 5:
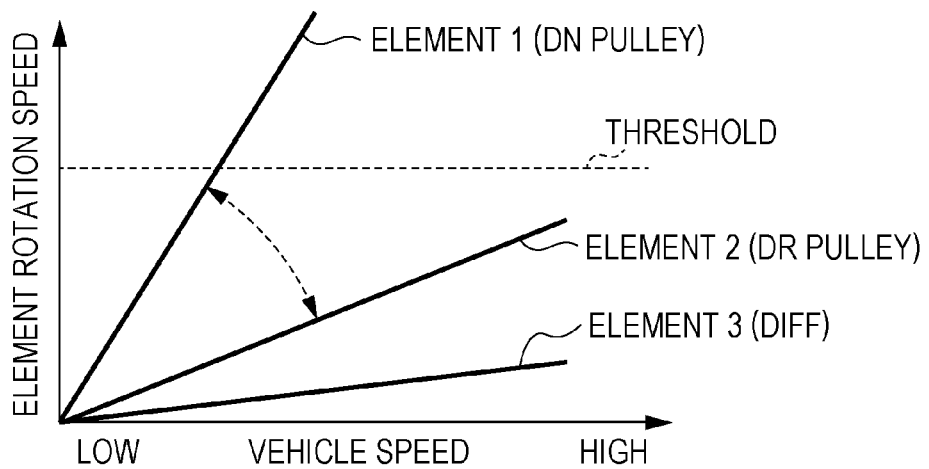
FIG. 5 is another explanatory drawing for the properties used in calculating the element rotation speed in FIG. 3.

FIGS. 4 and 5 are the drawings for explaining properties of the element rotation speed. In FIGS. 4 and 5, element rotation speeds refers to rotation speeds of various elements (portions) of the transmission 10, specifically, rotation speeds of the DR pulley 30, the DN pulley 32, and differential mechanism (indicated by "diff" in the drawings) 46 (more specifically, a ring gear thereof) of the CVT mechanism 26.

FIG. 4 indicates properties in a case where the gear ratio of the CVT mechanism 26 is at a LOW end, and FIG. 5 indicates properties in a case where the gear ratio thereof is at an over drive (OD) end. Element 1 is the DR pulley 30 and element 2 is the DN pulley 32 when the gear ratio is at the LOW end and vice versa when the gear ratio is at the OD end.

In step S106, element rotation speed is calculated on the basis of the vehicle speed (horizontal axis) detected by the rotational speed sensor 66 and the current gear ratio set in the CVT mechanism 26, according to the property of FIG. 4 or 5 if the gear ratio is at the LOW end or the OD end, whereas if the gear ratio is between the LOW end and the OD end, element rotation speed is calculated in accordance with the property set between the properties of FIGS. 4 and 5, as illustrated by broken lines. Specifically, the element rotation speed is calculate by obtaining the intersection of each of three kinds of properties, elements 1, 2, and 3, and then reading the value of the vertical axis corresponding to the intersection.

As described above, a concept of "element rotation speed" is introduced in the deterioration determination of the embodiment, and the element rotation speed is calculated in the processing of step S106. The concept of element rotation speed will be discussed later.

Then, the process proceeds to step S108 in the flowchart of FIG. 3 to determine whether or not the calculated element rotation speed (the rotation speed of each of the rotation elements (the DR pulley 30, the DN pulley 32, and the differential mechanism 46 of the CVT mechanism 26) of the transmission 10) is equal to or greater than a threshold (shown in FIGS. 4 and 5). If NO, the process proceeds to step S104. If YES, the process proceeds to step S110 to determine whether or not the oil temperature of the automatic transmission fluid detected in step S102 is equal to or higher than a predetermined temperature, and measure the duration of a state in which the element rotation speed is determined to be equal to or greater than the threshold in step S108.

Then, the process proceeds to step S112 to determine whether or not the duration measured in step S110 is equal to or longer than a predetermined time period, which is set as appropriate. If NO, the process proceeds to step S104. If YES, the process proceeds to step S114, and it is considered (determined) that the mode is the deterioration determination identification mode.

As described above, if it is determined that the detected oil temperature of the automatic transmission fluid is equal to or higher than the predetermined temperature in step S102, that the element rotation speed is equal to or greater than the threshold in step S108, and that the state continues over the predetermined time period, which is set as appropriate, or longer in step S112, the deterioration determination device 62A determines that the mode is the deterioration determination identification mode, that is, the deterioration determination device 62A determines that the predetermined condition is established.

As a result, in the flowchart of FIG. 2, the determination of step S10 is affirmed and the process proceeds to step S12 to calculate the rate of increase in oil temperature.

Figure 6:
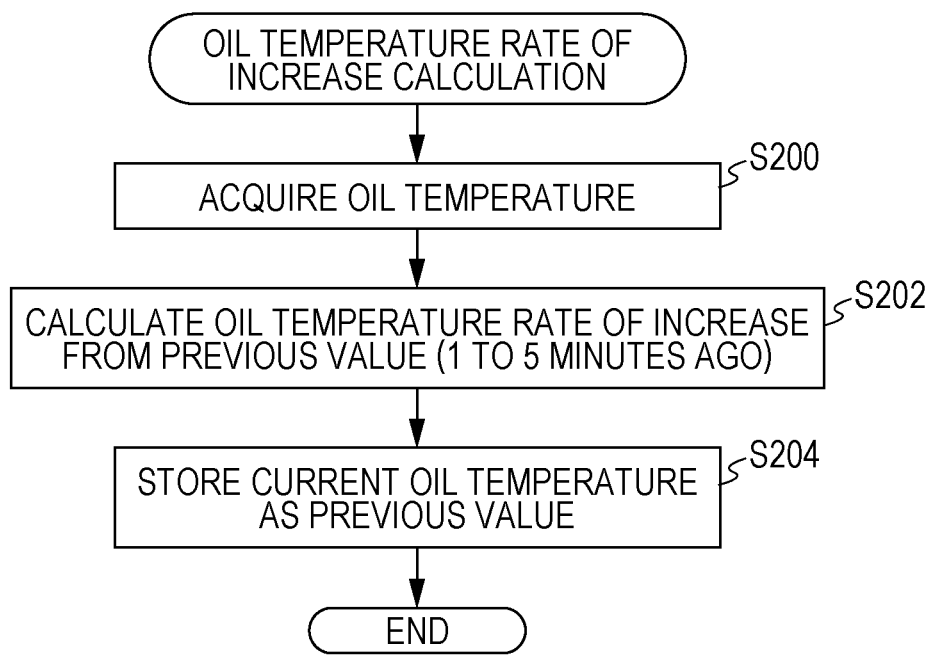
FIG. 6 is a subroutine flowchart of the flowchart of FIG. 2, illustrating processing for calculating rate of increase in oil temperature.

FIG. 6 is a subroutine flowchart illustrating processing for the calculation.

In step S200, the oil temperature of the ATF 60 detected by the oil temperature sensor 64 is acquired (read) again by an oil temperature rate of increase calculator 62B in the ECU 62. Then, the process proceeds to step S202, and the oil temperature rate of increase calculator 62B calculates the rate of increase in oil temperature by obtaining a difference value (or a differentiated value) from a previous value (a value of, for example, 1 to 5 minutes ago), and then the process proceeds to step S204 to store the calculated value as a previous value for a next calculation.

Now, the process returns to the flowchart of FIG. 2 and proceeds to step S14, and a threshold calculator 62C in the ECU 62 calculates a threshold (a threshold for estimating degradation of defoaming performance) which is used to compare with the rate of increase in oil temperature.

Figure 7:
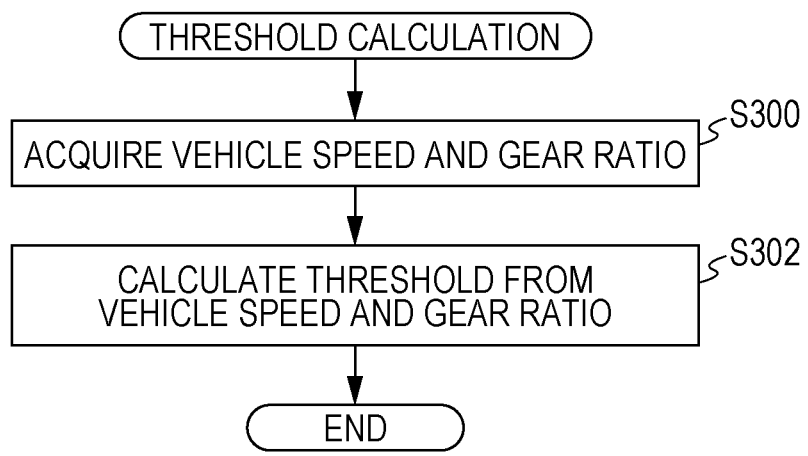
FIG. 7 is a subroutine flowchart of the flowchart of FIG. 2, illustrating processing for calculating threshold.

FIG. 7 is a subroutine flowchart illustrating processing for the calculation.

In step S300, the threshold calculator 62C acquires (reads) the vehicle speed and the gear ratio again. Then, the process proceeds to step S302, and the threshold calculator 62C calculates a threshold by searching the property illustrated in FIG. 8 based on the acquired vehicle speed and the gear ratio.

Figure 8:
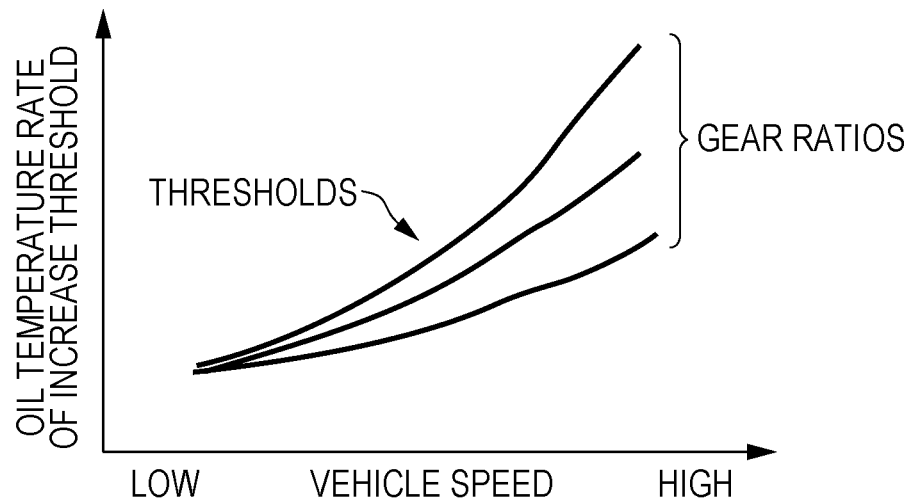
FIG. 8 is an explanatory drawing for the properties used in calculating the threshold in FIG. 7.

As illustrated in FIG. 8, a threshold is set for each gear ratio and is set so as to increase as the vehicle speed increases. This is because, as the vehicle speed increases, the degree of agitation of the ATF 60 in the transmission case 52 increases and thereby friction increases, and thus, it is estimated that defoaming performance thereof is degraded. Three lines illustrated in FIG. 8 are set in such a manner that an upper line has a higher gear ratio.

Now, the process returns to the flowchart of FIG. 2 and proceeds to step S16, and the deterioration determination device 62A compares the oil temperature rate of increase calculated in S12 with the threshold calculated in S14. Then the deterioration determination device 62A determines whether or not the oil temperature rate of increase calculated in S12 is equal to or greater than the threshold calculated in S14. If NO, subsequent processing will be skipped. If YES, the process proceeds to step S18 to determine that the ATF 60 is deteriorated, and a change urging device 62D in the ECU 62 illuminates a warning lamp indicating a need to change the ATF to notify a user to change the ATF 60.

Note that, in step S18, as an alternative to illuminating the ATF change warning lamp, the change may be urged sonically by using an audio device, or graphically (or more preferably sonically and graphically) by using a screen of a navigation device.

Figure 9:
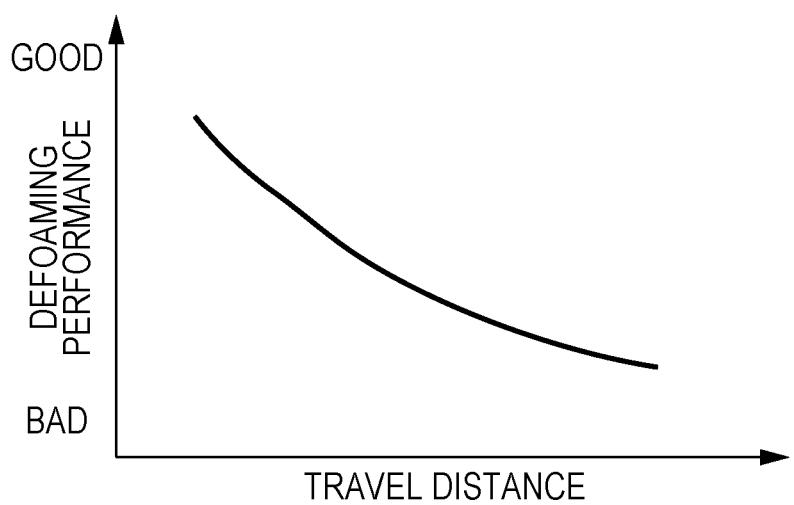
FIG. 9 is an explanatory drawing for the property of defoaming performance with respect to travel distance of the automatic transmission fluid illustrated in FIG. 1.
Figure 10:
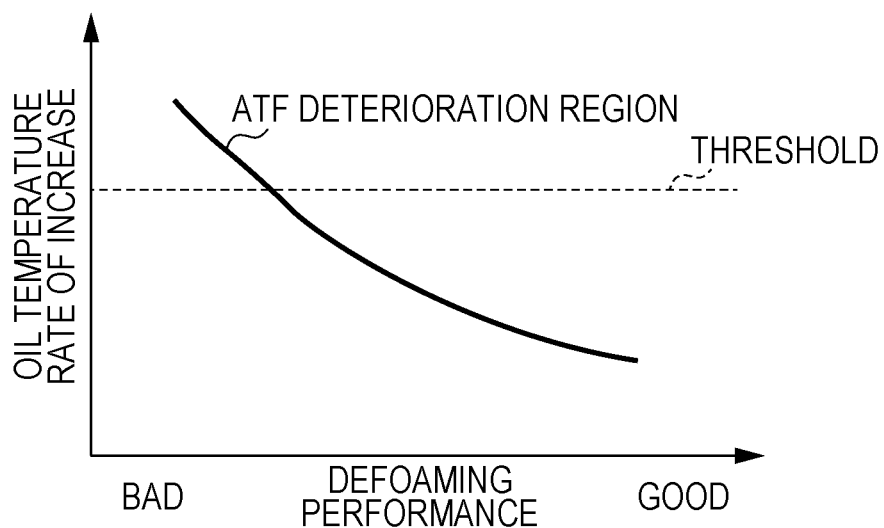
FIG. 10 is an explanatory drawing for the property of rate of increase in oil temperature with respect to the defoaming performance illustrated in FIG. 9.

Now, the deterioration determination described above will be explained with reference to FIGS. 9 to 12. It is well known that as the travel distance increases, the defoaming performance of the ATF 60 is degraded, as illustrated in FIG. 9, and that as the defoaming performance is degraded, the rate of increase in oil temperature of the ATF 60 increases, as illustrated in FIG. 10.

However, determination of the deterioration cannot be made promptly simply by comparing the rate of increase in oil temperature of the ATF 60 with the threshold.

For this reason, the present inventor performed further research and found that deterioration of the ATF 60 can be determined accurately by calculating a threshold sufficient for estimating degradation of the defoaming performance (in other words, deterioration of the ATF 60) on the basis of a travel condition of the vehicle, determining whether or not a deterioration determination is possible by determining establishment of a predetermined condition, and, if it is determined that the deterioration determination is possible, comparing the threshold with the calculated oil temperature rate of increase, and thereby the inventor arrived at the embodiment.

Figure 11:
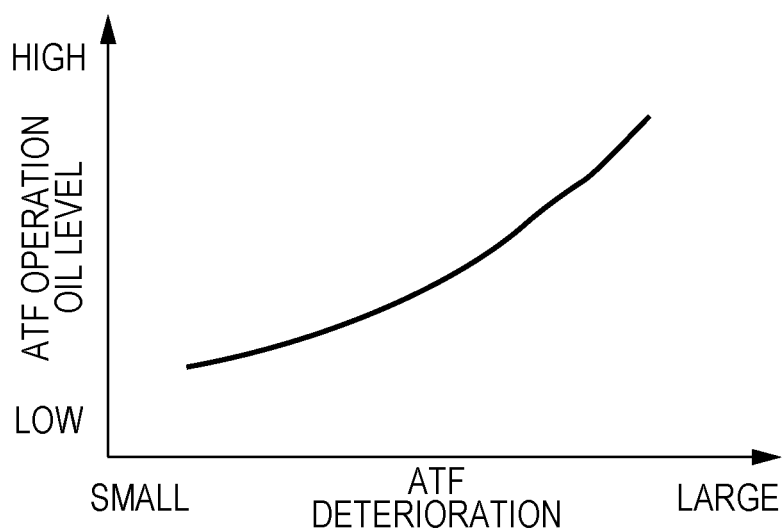
FIG. 11 is an explanatory drawing for the property of an operation oil level with respect to the deterioration of the automatic transmission fluid illustrated in FIG. 1.
Figure 12:
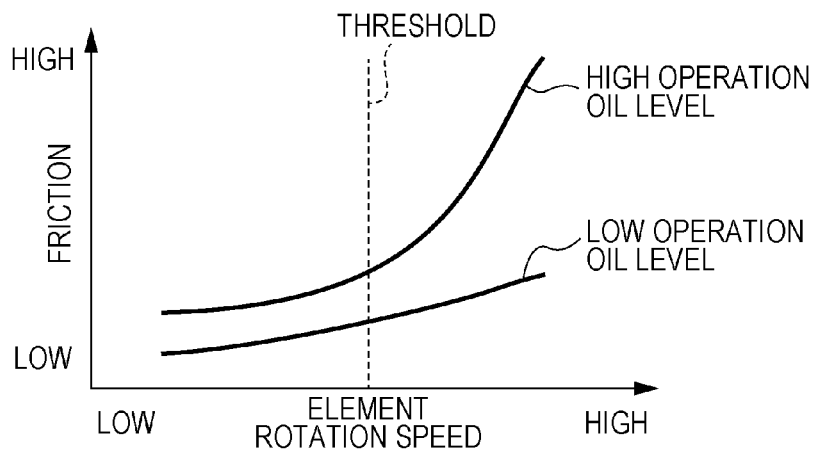
FIG. 12 is an explanatory drawing for the properties of friction of the automatic transmission fluid with respect to the element rotation speed of the automatic transmission of FIG. 1.

More specifically, on the basis of a finding that, as the deterioration of the ATF 60 progresses, the level of operation oil (a foaming oil level of the ATF 60 during operation of the transmission 10 in the transmission case 52) is increased, as illustrated in FIG. 11, the determination is configured in such a manner that, because the level of operation oil cannot be grasped directly, a concept of element rotation speed is introduced as an alternative as illustrated in FIG. 12, and, because agitation resistance is predicted to increase in a condition where the level of the operation oil is high, the element rotation speed is used as a trigger.

That is, a condition, where the oil temperature is relatively high and where there exists for a predetermined time period, which is set as appropriate, a state in which the calculated rotation speed is equal to or greater than the threshold, is used as a deterioration determination identification mode in which a deterioration determination can be made, and deterioration of the ATF 60 is determined when the mode is the deterioration determination identification mode. With this configuration, deterioration of the ATF 60 can be determined accurately.

Figure 13:
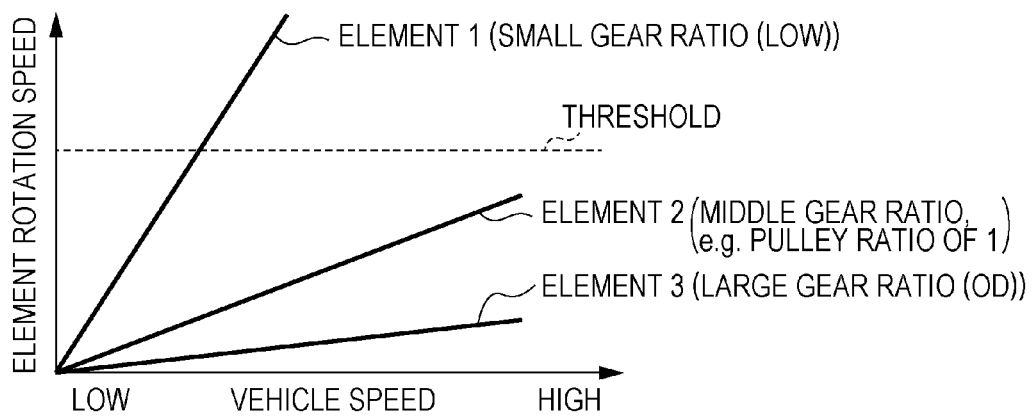
FIG. 13 is an explanatory drawing for the modified properties used in calculating the element rotation speed in FIG. 3.

Note that, in the above explanations, the properties illustrated in FIGS. 4 and 5 are provided for calculating the element rotation speed; however, the properties are not limited thereto, and the elements may be of, for example, the differential mechanism 46 (specifically, a ring gear thereof), in which a degree of agitation (stirring up) of the ATF 60 (in other words, the friction of the ATF 60) is large, and as illustrated in FIG. 13, element 1 may be set to indicate rotation speed of the differential mechanism 46 when the gear ratio of the CVT mechanism 26 is small (LOW), element 2 may be set to indicate rotation speed thereof when the gear ratio is in the middle, such as when a pulley ratio is 1, and element 3 may be set to indicate rotation speed thereof when the gear ratio is large (OD).

As described above, in the embodiment, the deterioration determination apparatus for the automatic transmission fluid (ATF) 60 for operation and lubrication of the automatic transmission 10, which is mounted in the vehicle, changes the speed of rotation of the drive source (engine) and transmits the changed rotation to drive wheels, and which is rotatably supported in the transmission case 52, is configured to include: an oil temperature detection unit (oil temperature sensor 64, ECU 62, S12, S200) that detects the oil temperature of the automatic transmission fluid; an oil temperature rate of increase calculation unit (ECU 62, S12, S202) that calculates the rate of increase in oil temperature detected by the oil temperature detection unit; a threshold calculation unit (ECU 62, S14, S300, S302) that calculates a threshold for estimating degradation of a defoaming property of the automatic transmission fluid on the basis of a travel condition of the vehicle; a deterioration determination unit (ECU 62, S16, S18) that, when a predetermined condition is determined to be established (S100, S102, S106 to S114), compares the calculated oil temperature rate of increase with the threshold, and, when the calculated oil temperature rate of increase is equal to or greater than the threshold, determines that the automatic transmission fluid is deteriorated; and a change urging unit (ECU 62, S18) that, when the deterioration determination unit determines that the automatic transmission fluid is deteriorated, urges the user to change the automatic transmission fluid, and therefore the deterioration of the ATF (automatic transmission fluid) 60 can be determined accurately with a simple configuration.

That is, on the basis of a finding that, as the rate of increase in oil temperature increases, the defoaming property of the ATF 60 is degraded and thus the ATF 60 is deteriorated, the determination is performed so as to calculate a threshold for estimating degradation of a defoaming property on the basis of a travel condition of the vehicle and compare the calculated oil temperature rate of increase with the threshold when a predetermined condition is determined to be established, and thereby deterioration of the automatic transmission fluid can be determined easily. In addition, processing for acquiring a plurality of deterioration elements related to various deterioration factors is not required, and thereby the cost of the apparatus can be reduced. Furthermore, by using this apparatus, the user can change the ATF 60 without delay.

The deterioration determination unit is configured so as to determine (ECU 62, S10, S102, S106 to S114) that the predetermined condition is established when the detected oil temperature of the automatic transmission fluid is equal to or higher than the predetermined temperature and when a state in which the rotation speed (element rotation speed) of a rotation element of the automatic transmission is equal to or greater than the threshold continues over a predetermined time period, and thereby deterioration of the automatic transmission fluid can be determined accurately.

That is, on the basis of a finding that the level of operation oil in the transmission case 52 increases as the deterioration of the ATF 60 progresses, when deterioration is determined by using rate of increase in oil temperature, the determination is performed so as to consider that a state in which the level of operation oil is high is a predetermined condition, that is, a state in which a deterioration determination can be made by using the oil temperature, rotation speed and duration, and compare the rate of increase in oil temperature and the threshold at that time, and thereby the deterioration of the automatic transmission fluid can be determined accurately.

The threshold calculation unit is configured so as to calculate (ECU 62, S14, S300, S302) the threshold on the basis of the travelling speed and the gear ratio of the vehicle, and therefore a travel condition of the vehicle can be reflected on the calculation of threshold for estimating degradation of a defoaming property of the automatic transmission fluid (ATF) 60, and thereby the deterioration of the automatic transmission fluid (ATF) 60 can be determined more accurately.

Note that, although the above description discloses a continuously variable transmission (CVT) as the automatic transmission, the automatic transmission is not limited thereto and may be a stepped transmission or a twin clutch transmission.

According to an aspect of an embodiment, a deterioration determination apparatus for an automatic transmission fluid for operation and lubrication of an automatic transmission, which is mounted in a vehicle, changes a speed of rotation of a drive source and transmits the changed rotation to drive wheels, and which is rotatably supported in a transmission case, is configured to include: an oil temperature detection unit that detects an oil temperature of the automatic transmission fluid; an oil temperature rate of increase calculation unit that calculates a rate of increase in oil temperature detected by the oil temperature detection unit; a threshold calculation unit that calculates a threshold for estimating degradation of a defoaming property of the automatic transmission fluid on the basis of a travel condition of the vehicle; a deterioration determination unit that, when a predetermined condition is determined to be established, compares the calculated oil temperature rate of increase with the threshold, and, when the calculated oil temperature rate of increase is equal to or greater than the threshold, determines that the automatic transmission fluid is deteriorated; and a change urging unit that, when the deterioration determination unit determines that the automatic transmission fluid is deteriorated, urges a user to change the automatic transmission fluid.

The deterioration determination unit may be configured to determine that the predetermined condition is established when the detected oil temperature of the automatic transmission fluid is equal to or higher than a predetermined temperature and when a state in which a rotation speed of a rotation element of the automatic transmission is equal to or greater than a threshold continues over a predetermined time period.

The threshold calculation unit may be configured to calculate the threshold on the basis of travelling speed and a gear ratio of the vehicle.

According to the aspect of the embodiment, the deterioration determination apparatus for the automatic transmission fluid is configured to detect the oil temperature of the automatic transmission fluid, calculate the rate of increase in the detected oil temperature, calculate a threshold for estimating degradation of a defoaming property of the automatic transmission fluid on the basis of a travel condition of the vehicle, compare the calculated oil temperature rate of increase with the threshold when a predetermined condition is determined to be established, and determine that the automatic transmission fluid is deteriorated when the calculated oil temperature rate of increase is equal to or greater than the threshold, and urge the user to change the automatic transmission fluid when it is determined that the automatic transmission fluid is deteriorated, and therefore the deterioration of the automatic transmission fluid can be determined accurately with a simple configuration.

That is, on the basis of a finding that, as the rate of increase in oil temperature increases, the defoaming property of the automatic transmission fluid is degraded and thus the automatic transmission fluid is deteriorated, the deterioration determination is performed so as to calculate a threshold for estimating degradation of a defoaming property (in other words, deterioration of the automatic transmission fluid) on the basis of a travel condition of the vehicle and compare the calculated oil temperature rate of increase with the threshold when a predetermined condition is determined to be established, and thereby deterioration of the automatic transmission fluid can be determined easily. In addition, processing for acquiring a plurality of deterioration elements related to various deterioration factors is not required, and thereby the cost of the apparatus can be reduced. Furthermore, by using this apparatus, the user can change the automatic transmission fluid without delay.

The deterioration determination apparatus according to the aspect of the embodiment may be configured so as to determine that the predetermined condition is established when the detected oil temperature of the automatic transmission fluid is equal to or higher than the predetermined temperature and when a state in which the rotation speed (element rotation speed) of a rotation element of the automatic transmission is equal to or greater than the threshold continues over a predetermined time period. In this case, deterioration of the automatic transmission fluid can be determined accurately.

That is, on the basis of a finding that the level of operation oil (the level of foamed oil during operation of the automatic transmission) of the automatic transmission oil in the transmission case increases as the deterioration of the automatic transmission fluid progresses, when deterioration is determined by using rate of increase in oil temperature, the deterioration determination is performed so as to consider that a state in which the level of operation oil is high is a predetermined condition, that is, a state in which a deterioration determination can be made by using the oil temperature, rotation speed and duration, and compare the rate of increase in oil temperature and the threshold at that time, and thereby the deterioration of the automatic transmission fluid can be determined accurately.

The deterioration determination apparatus according to the aspect of the embodiment may be configured so as to calculate the threshold on the basis of the travelling speed and the gear ratio of the vehicle. In this case, a travel condition of the vehicle can be reflected on the calculation of threshold, and thereby the deterioration of the automatic transmission fluid can be determined more accurately.

Obviously, numerous modifications and variations of the present invention are possible in light of the above teachings. It is therefore to be understood that within the scope of the appended claims, the invention may be practiced otherwise than as specifically described herein.

What is claimed is:

1. A deterioration determination apparatus comprising:
    an oil temperature detector configured to detect an oil temperature of oil for lubrication of a transmission in a vehicle;
    an oil temperature rate of increase calculator configured to calculate a rate of increase in the oil temperature detected by the oil temperature detector;
    a threshold calculator configured to calculate, based on a travel condition of the vehicle, a first threshold for estimating degradation of a defoaming property of the oil; and
    a deterioration determination device configured to compare the rate of increase in the oil temperature with the first threshold and to determine that the oil is deteriorated when the rate of increase in the oil temperature is equal to or higher than the first threshold,
    wherein the threshold calculator is configured to change the first threshold based on a change in a travel speed of the vehicle or a change of a gear ratio of the vehicle.

2. The deterioration determination apparatus according to claim 1, further comprising a change urging device configured to notify a user to change the oil when the deterioration determination device determines that the oil is deteriorated.

3. The deterioration determination apparatus according to claim 1, wherein when the deterioration determination device determines that a predetermined condition is established, the deterioration determination device compares the oil temperature rate of increase with the first threshold.

4. The deterioration determination apparatus according to claim 3, wherein the predetermined condition includes that the oil temperature detected by the oil temperature detector is equal to or higher than a predetermined temperature and that a state where a rotation speed of a rotation element of the transmission is equal to or greater than a second threshold continues over a predetermined time period.

5. The deterioration determination apparatus according to claim 1, wherein the threshold calculator calculates the first threshold based on the travel speed of the vehicle and the gear ratio of the vehicle.

6. The deterioration determination apparatus according to claim 5, further comprising a rotational speed detector configured to detect the travel speed.

7. The deterioration determination apparatus according to claim 5, further comprising a continuously variable transmission device configured to set the gear ratio.

8. The deterioration determination apparatus according to claim 1, wherein the threshold calculator is configured to increase the first threshold based on an increase in the travel speed of the vehicle or an increase of the gear ratio of the vehicle.

9. The deterioration determination apparatus according to claim 1, wherein when the deterioration determination device determines that a predetermined condition is established, the deterioration determination device compares the oil temperature rate of increase with the first threshold, and
wherein when the deterioration determination device determines that the predetermined condition is not established, the deterioration determination device does not compare the oil temperature rate of increase with the first threshold.

10. A deterioration determination method comprising:
detecting an oil temperature of oil for lubrication of a transmission in a vehicle;
calculating a rate of increase in the oil temperature;
calculating, based on a travel condition of the vehicle, a first threshold for estimating degradation of a defoaming property of the oil;
changing the first threshold based on a change in a travel speed of the vehicle or a change of a gear ratio of the vehicle;
comparing the rate of increase in the oil temperature with the first threshold; and
determining that the oil is deteriorated when the rate of increase in the oil temperature is equal to or higher than the first threshold.

11. The deterioration determination method according to claim 10, wherein when a predetermined condition is established the comparing is performed.

12. The deterioration determination method according to claim 11, wherein the predetermined condition includes that the oil temperature is equal to or higher than a predetermined temperature and that a state where a rotation speed of a rotation element of the transmission is equal to or higher than a second threshold continues over a predetermined time period.

13. The deterioration determination method according to claim 10, further comprising notifying a user to change the oil when the oil is deteriorated.

14. The deterioration determination method according to claim 10, wherein the changing the first threshold includes increasing the first threshold based on an increase in the travel speed of the vehicle or an increase of the gear ratio of the vehicle.

15. The deterioration determination method according to claim 10, wherein when a predetermined condition is established the comparing is performed, and
wherein when the predetermined condition is not established the comparing is not performed.

16. A deterioration determination apparatus comprising:
an oil temperature detection means for detecting an oil temperature of oil for a transmission in a vehicle;
an oil temperature rate of increase calculation means for calculating a rate of increase in the oil temperature detected by the oil temperature detection means;
a threshold calculation means for calculating, based on a travel condition of the vehicle, a first threshold for estimating degradation of a defoaming property of the oil, and for changing the first threshold based on a change in a travel speed of the vehicle or a change of a gear ratio of the vehicle; and
a deterioration determination means for comparing the rate of increase in the oil temperature with the first threshold and for determining that the oil is deteriorated when the rate of increase in the oil temperature is equal to or higher than the first threshold.

17. The deterioration determination apparatus according to claim 16, wherein the threshold calculator means is configured to increase the first threshold based on an increase in the travel speed of the vehicle or an increase of the gear ratio of the vehicle.

18. The deterioration determination apparatus according to claim 16, wherein when the deterioration determination means determines that a predetermined condition is established, the deterioration determination means compares the oil temperature rate of increase with the first threshold, and
wherein when the deterioration determination means determines that the predetermined condition is not established, the deterioration determination means does not compare the oil temperature rate of increase with the first threshold.

* * * * *